United States Patent [19]

Kudoh et al.

[11] Patent Number: 4,511,748

[45] Date of Patent: Apr. 16, 1985

[54] PROCESS FOR PRODUCING ALKYLBENZENES

[75] Inventors: Michio Kudoh, Yohohama; Mitsuo Matsuno, Kawasaki; Hirosuke Imai, Yohohama, all of Japan

[73] Assignee: Nippon Oil Co., Ltd., Tokyo, Japan

[21] Appl. No.: 613,211

[22] Filed: May 23, 1984

[30] Foreign Application Priority Data

May 31, 1983 [JP] Japan ................................. 58-96756

[51] Int. Cl.$^3$ ................................................ C07C 3/52
[52] U.S. Cl. ..................................... 585/467; 585/446; 585/448; 502/200; 502/344
[58] Field of Search .................. 585/446, 448, 467; 502/200, 344

[56] References Cited

U.S. PATENT DOCUMENTS

| | | | |
|---|---|---|---|
| 2,448,641 | 9/1948 | Whitman | 585/467 |
| 2,836,633 | 5/1958 | Esmay et al. | 585/467 |
| 2,916,532 | 12/1959 | Schmerling et al. | 585/446 |
| 3,701,814 | 10/1972 | Shilling | 585/467 |
| 4,388,480 | 6/1983 | Imai et al. | 585/516 |

FOREIGN PATENT DOCUMENTS

| | | | |
|---|---|---|---|
| 695073 | 9/1964 | Canada | 585/467 |
| 4933181 | 6/1969 | Japan | 585/438 |
| 5108932 | 3/1971 | Japan | 585/467 |

*Primary Examiner*—Delbert E. Gantz
*Assistant Examiner*—A. Pal
*Attorney, Agent, or Firm*—Saidman, Sterne, Kessler & Goldstein

[57] ABSTRACT

A process is disclosed for producing alkylbenzenes by the alkylation of aromatic hydrocarbons with olefins. High reactivity and selectivity are afforded by the use of a catalyst comprising sodium and/or sodium amide deposited on a carrier represented by the formula $K_2O \cdot x\, Al_2O_3$ where x is $0.5 \leq x \leq 11$.

6 Claims, No Drawings

PROCESS FOR PRODUCING ALKYLBENZENES

BACKGROUND OF THE INVENTION

1. Field of the Invention

This invention relates to a process for the production of alkylbenzenes and more particularly to a process which comprises alkylating an aromatic hydrocarbon containing a side-chain in which at least one hydrogen atom is bonded to a carbon atom alpha to the nucleus with an olefin in the presence of a novel catalyst.

2. Prior Art

It is known to produce alkylbenzenes by reacting a benzene with an alkylhalide or corresponding olefin in the presence of a Friedel-Crafts catalyst. This reaction however has often resulted in mixtures containing numerous isomers, which in turn required precise fractionation to give a selected product.

Another process is known for the production of alkylbenzenes in which aromatic hydrocarbons are reacted with olefins in the presence of an alkali metal such as lithium, sodium and potassium, as reported for example by H. Pines et al in the Journal of American Chemical Society, 78 4316 (1956).

British Pat. No. 1,269,280 discloses alkylating an aromatic hydrocarbon with a mono-olefin in the presence of a catalyst prepared by dispersing an alkyl metal on a potassium compound.

Such prior art processes using alkali metal catalysts involve less isomers than would be the case with Friedel-Crafts catalysts, but have a drawback in that aromatics reactivity is low and intended alkylbenzenes selectivity is also low due to large amounts of by-produced isomeric alkylbenzenes and olefinic dimers. The aforementioned catalysts are mostly prolonged in reaching maximum activity, requiring so much time to stabilize the reaction. Furthermore, they would often induce polymerization reactions with resultant polymers deposited on the catalyst surfaces to slowly deplete the catalytic activity. Concomitant with reduced catalytic activity, product selectivity tends to decline. Most deactivated catalysts would become solidified with resinous polymers within the reactor, but part of them remain still active which would cause explosion or fire on contact with oxygen or moisture in the atmosphere when removing the catalyst for replacement.

The prior art catalysts contain less than 5 weight percent, or usually only 1–3 weight percent of sodium or potassium that can be deposited on the carrier due to this carrier being inert and small in porosity rate. Attempts to deposit more than 5 weight percent of such alkali metals would result in muddy coagulates on the carrier surfaces, leading to loss of catalytic activity.

SUMMARY OF THE INVENTION

Whereas, the present invention provides an improved process for the production of alkylbenzenes by side-chain alkylation of aromatic hydrocarbons, which process will eliminate the above-mentioned drawbacks of the prior art.

The process according to the invention enables the production of alkylbenzenes with increased rate of yields and at high selectivity as will appear clear from the following detailed description.

More specifically, the process of the invention is characterized by the use of a novel catalyst comprising sodium and/or sodium amide supported on a carrier of the formula $$K_2O \cdot xAl_2O_3$$

where x is $0.5 \leq x \leq 11$ in the reaction of an aromatic hydrocarbon with an olefin, said aromatic hydrocarbon containing a side-chain in which at least one hydrogen atom is bonded to a carbon atom alpha to the nucleus. It has now been also found that the catalyst of the invention permits initiation of the reaction almost instantly as the aromatic hydrocarbon and the olefin are charged; that is, there is substantially no induction or blank period prior to the start of the reaction, and further that the above formulated carrier can readily absorb and maintain adequate amounts of alkali metals in well dispersed form.

DETAILED DESCRIPTION

The class of olefins eligible for the invention includes compounds of normally 2–20 carbon atoms such as for example ethylene, propylene, 1-butene, cis- and trans-2-butene, 1-pentene, 3-methyl-1-pentene, 1-hexene, cis- and trans-2- or 3-hexene, 4-methyl-1-pentene, 4-methyl-2-pentene, dodecene and hexadecene of which ethylene and propylene are most preferred.

The aromatic hydrocarbon with a side-chain of 1–6 carbon atoms containing at least one hydrogen on a carbon atom alpha to the nucleus, which is suitable for the process of the invention includes toluene, ethylbenzene, cumene, n-propylbenzene, sec-butylbenzene, isobutylbenzene, n-butylbenzene, o-, m- and p-xylenes, mesitylene, pseudo-cumene, durene, isodurene, p-diisopropylbenzene, alpha- and beta-methylnaphthalene and dimethyl naphthalenes.

The above olefins and aromatic hydrobarbons may not necessarily be of high purity, but are suitably free of as much unintended olefins, diolefins, aromatics, water, air or carbonic acid gas as can be removed industrially feasibly. Ethane, propane, butane or other saturated hydrocarbons should preferably be absent, but if present, would pose no particular problem.

Typical reactions for alkylbenzene production are the alkylation of toluene with ethylene or propylene to give n-propylbenzene or isobutylbenzene respectively, and of ethylbenzene with propylene to give 2-methyl-3-phenylbutane. These alkylbenzenes find useful application as intermediates to give pharmaceuticals, agricultural chemicals and perfumes.

The compounds represented by the formula $K_2O \cdot xAl_2O_3$ are used as a carrier according to the invention for supporting thereon sodium and/or sodium amide. The $K_2O \cdot xAl_2O_3$ compound is prepared by the reaction of a potassium-containing compound with an aluminum-containing compound. The potassium-containing compound includes KOH, $KOR^I$ ($R^I$ is at least one member of the group consisting of straight-chain or branched aliphatic hydrocarbon moieties of 1–20 carbon atoms, aryl and aralkyl groups of 6–30 carbon atoms), $KHCO_3$, $K_2CO_3$ (including those containing crystal water), KH, and $KR^{II}$ ($R^{II}$ is at least one member of the group consisting of straight-chain or branched aliphatic hydrocarbon moieties of 1–20 carbon atoms, aryl and aralkyl groups of 6–30 carbon atoms). The aluminum-containing compound includes alumina hydrates such as hydrargillite, bayerite, boehmite and diaspore, $\alpha$- and $\gamma$-alumina, and $A(OR^{III})_3$ ($R^{III}$ is at least one member of the group consisting of straight-chain or branched aliphatic hydrocarbon moieties of 1–20 carbon atoms, aryl and aralkyl groups of 6–30 carbon atoms). One or more of the potassium-containing compounds and of the aluminum-containing compounds are blended in a potassium (K)/aluminum (Al) ratio which is within the range of $K_2O \cdot xAl_2O_3$ where x is $0.5 \leq x \leq 11$, preferably $1 \leq x \leq 5$. The blend is reacted usually at 400°–2,000° C., preferably 500°–1,500° C. for 1–20 hours in the presence or absence of air or nitrogen.

The carrier according to the invention is only conveniently represented by the above formula in which potassium oxide and alumina appear as the constituents. However, these two materials exist mostly as complex oxides and vary in their compositions from one source to another. Mere blends of them therefore do not give such catalytic activity and selectivity characteristics that are provided by the invention.

The catalyst according to the invention may be suitably used in a flow mode of reaction using a fixed bed, or in a completely mixed mode of reaction with a reactor disposed for a continuous charge of both catalyst and starting reactants.

The amount of sodium and/or its compounds to be deposited on the $K_2O \cdot xAl_2O_3$ carrier is preferably 0.1–20 weight percent in terms of sodium atoms. It has now been found that in spite of such large sodium deposits as 20 wt. %, this metal can be finely dispersed and can literally exhibit so much high reactivity as well as good selectivity without tarry or resinous materials and with excellent resistance to moisture or other impurities in the reaction system and hence for a prolonged period of service life. Amounts of the alkali metal as low as 0.1–1 wt. % may decline somewhat in activity but are of course allowable for the practice of the invention. However, most suitable amounts of the alkali metal as used in the invention are 1–15 wt. %.

Sodium may be supported on the carrier by mixing both of these catalyst components with stirring in the absence of a solvent at a temperature exceeding the melting point of sodium, e.g. 120°–400° C., or by deposition of sodium vapor, or by mixing and quickly stirring the two components in a high boiling solvent such as white oil at a temperature above the melting point of sodium. To support sodium amide on the carrier, this may be done by preparing an ammonium solution of sodium amide and impregnating the carrier with this solution at 0°–200° C., with subsequent evaporation of the ammonium.

While the exact structure of the sodium metal or sodium amide deposited carrier is not clearly known, it is believed that part of the sodium atoms are physically and chemically adsorbed onto the carrier surfaces and further substituted with those atoms which constitute the carrier.

The particle size of the carrier is variable between 0.1 mm and 10 mm depending on the form and capacity of the reactor used. The desired particulate material may be obtained by calcining, pulverizing and classifying the carrier or by first kneading and granulating the starting material and then calcining the same.

The process of the invention is carried out suitably at a temperature range of 100°–250° C., preferably 100°–180° C. and at a pressure range of 10–100 kg./cm².

The aromatic hydrocarbon to olefin molar ratio is suitably in the range of 0.5–10, preferably 1–5. Smaller ratios than 0.5 would result in increased dimers and hence reduced alkylbenzene selectivity. Conversely, larger ratios than 10 would result in reduced yields of alkylbenzene.

There may be considered various modes of reaction to implement the invention. For example, a batch or semi-batch operation using an autoclave is suitable. A complete continuous mode of reaction may be employed with an autoclave to which the catalyst and the starting reaction materials are charged continuously. Another eligible mode of reaction is to use a fixed-bed reactor charged with the catalyst through which the starting materials are passed.

When using an autoclave, the amount of the catalyst with respect to the aromatic hydrocarbon is not particularly limited but may be practically from 0.5 to 20 weight percent. By the amount of the catalyst is meant the sum of the carrier and the deposited sodium and/or sodium compound.

The reaction time for batch or semi-batch or the retention time for the continuous process is suitably in the range of 0.1–10 hours. For the fixed-bed process, the liquid hourly space velocity (L.H.S.V) is suitably in the range of 0.1–10 (V/V.hr).

Any of the above stated modes of reaction may be carried out in the presence of solvents such as heptane, octane, dodecane or mixtures thereof, or other compounds which will not induce objectionable side-reactions.

The invention will now be further described by way of the following examples which are provided for purposes of illustration but not for limiting the invention thereto.

INVENTIVE EXAMPLE 1

The reaction proceeds as follows:

$$KOH + \text{boehmite} \longrightarrow K_2O \cdot x\, Al_2O_3\; (x = 0.98) \xrightarrow{Na}$$

$$Na \text{ deposited } K_2O \cdot x\, Al_2O_3 \ldots *1$$

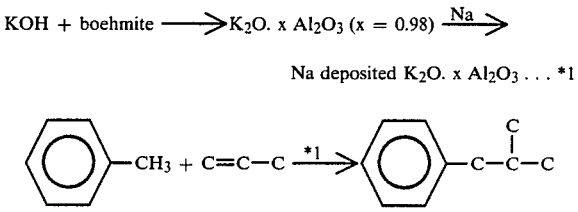

66 grams of sodium hydroxide pellets (cotaining 15% water) were comminuted and admixed with 80 grams of boehmite. The admixture was placed in an alumina melting pot and calcined in an air atmosphere at 1,200° C. for 5 hours. The thus calcined product upon cooling was taken into an alumina pot and further comminuted by a centrifugal ball mill for 2 hours. 60 grams of the resulting carrier having a particle size smaller than 60 mesh was charged to a 300 ml, 3-necked flask and heated at 150° C. in a nitrogen atmosphere, followed by stirring with addition of 6 grams sodium. The temperature was raised to 200° C., and stirring was continued for another hour to permit uniform deposition of sodium on the carrier.

The resulting catalyst was used for the synthesis of isobutylbenzene. To 1,000 ml stainless steel magnetic induction type autoclave equipped with stirrer were charged 16 grams catalyst, 390 grams toluene and 60 grams propylene. The reaction was effected at 160° C. and continued for 3 hours. The autoclave was quenched by tap water to terminate the reaction, followed by trapping unreacted propylene in a dry ice-methanol bath. Unreacted toluene and reaction products in the reactor were recovered by vacuum distillation. The recovered reaction liquid plus residues resulting from evaporation of the trapped propylene and having a boiling point higher than propylene dimers were analyzed by gas chromatography using a 0.25φx50 m caterpillar column of liquid silicon OV-101 thereby indicating propylene reactivity to be 59.7% and isobutylbenzene selectivity to be 85.6 mol % (based on propylene). Reaction data of this example are shown in Table 1 together with those of Comparative Examples 1 and 2.

Comparative Example 1

The reaction procedure of Inventive Example 1 was followed except that 23 grams potassium was used as the catalyst.

Comparative Example 2

The procedure of Inventive Example 1 was followed except that 33 grams catalyst comprising particulate $K_2CO_3$ and 5 wt. % sodium deposited thereon was used.

Inventive Example 2

The procedure of Inventive Example 1 was followed except that 400 grams ethylbenzene and 65 grams propylene were used. Analysis showed propylene reactivity to be 52.1% and 2-methyl-3-phenylbutane selectivity to be 83.8% (based on propylene).

Comparative Example 3

The procedure of Inventive Example 2 was followed except that 33 grams catalyst comprising particulate $K_2CO_3$ and 5 wt. % sodium deposited thereon was used. Analysis showed 23.0% propylene reactivity and 73.4% 2-methyl-3-phenylbutane selectivity (based on propylene).

Inventive Example 3

16 grams catalyst of Inventive Example 1 and 400 grams toluene were charged to an autoclave of the type described in Inventive Example 1. The system was pressured with ethylene to 40 KG./cm², and the reaction was effected at 150° C. and continued for 3 hours at that pressure maintained by ethylene charge. Unreacted ethylene was removed, and the reaction product was analyzed with the results that toluene reactivity was 76% and n-propylbenzene selectivity was 98.7%, with 1.3% indane. No 3-phenylpentane was found which would be otherwise formed when sodium is used.

TABLE 1

| | Inventive Example 1 | Comparative Example 1 | Comparative Example 2 |
| --- | --- | --- | --- |
| K (or Na), mol | 0.07 | 0.06 | 0.07 |
| toluene, mol | 4.24 | 4.00 | 4.52 |
| propylene, mol | 1.33 | 1.26 | 1.37 |
| reaction temperature, °C. | 160 | 160 | 160 |
| reaction time, hr | 3 | 3 | 3 |
| propylene reacting, % | 59.7 | 18.3 | 26.2 |
| $C_6$ selecting, mol % | 1.5 | 19.0 | 11.2 |
| $C_{10}$ selecting, mol % isobutylbenzene | 94.5 | 68.9 | 85.3 |
| n-butylbenzene, molar ratio | 9.5 | 8.1 | 8.6 |
| isobutylbenzene yield Amount of propylene reacted, mol % | 85.6 | 60.1 | 76.4 |

What is claimed is:

1. A process for the production of alkylbenzenes which comprises alkylating an aromatic hydrocarbon containing a side-chain in which at least one hydrogen atoms is bonded to a carbon atom alpha to the nucleus with an olefin in the presence of a catalyst comprising sodium and/or sodium amide deposited on a carrier of the formula $$K_2O.xAl_2O_3$$

where x is $0.5 \leq x \leq 11$.

2. A process according to claim 1 wherein said side-chain is of a carbon number ranging from 1 to 6.

3. A process according to claim 1 wherein said olefin is of a carbon number ranging from 2 to 20.

4. A process according to claim 1 wherein toluene as said aromatic hydrocarbon is reacted with propylene as said olefin thereby producing isobutylbenzene.

5. A process according to claim 1 wherein said carrier is prepared by reacting a potassium-containing compound selected from the group consisting of KOH, $KOR^I$, where $R^I$ is at least one member of the group consisting of straight-chain or branched aliphatic hydrocarbon moieties of 1-20 carbon atoms, aryl and aralkyl groups of 6-30 carbon atoms, $KHCO_3$, $K_2CO_3$, including those containing crystal water, KH, and $KR^{II}$, where $R^{II}$ is at least one member of the group consisting of straight-chain or branched aliphatic hydrocarbon moieties of 1-20 carbon atoms, aryl and aralykyl groups of 6-30 carbon atoms, with an aluminum-containing compound selected from the group consisting of alumina hydrates (α- and γ-alumina, and Al $(OR^{III})_3$, where $R^{III}$ is at least one member of the group consisting of straight-chain or branched aliphatic hydrocarbon moieties of 1-20 carbon atoms, aryl and aralkyl groups of 6-30 carbon atoms, at 400°-2,000° C. for 1-20 hours in the presence or absence of air or nitrogen, said potassium-containing compound being blended with said aluminum-containing compound in a ratio of K/A which is within the range of $K_2O.xAl_2O_3$ where x is $0.5 \leq x \leq 11$.

6. A process according to claim 5, wherein said alumina hydrates are selected from the group consisting of hydrargillite, bayerite, boehmite and diaspore.

* * * * *